United States Patent [19]

Umezawa et al.

[11] 4,415,657
[45] Nov. 15, 1983

[54] PROCESS FOR PREPARATION OF AN OPTICALLY ACTIVE MONOALKYL ESTER OF β-(S)-AMINOGLUTARIC ACID

[75] Inventors: Hamao Umezawa, Tokyo; Masaji Ohno, Kamakura; Junzo Hasegawa; Shigeki Hamaguchi, both of Akashi; Masahiro Ogura, Ono; Hajime Kawaharada, Kakogawa; Kiyoshi Watanabe, Akashi, all of Japan

[73] Assignee: Kanegafuchi Chemical Industry Company, Limited, Osaka, Japan

[21] Appl. No.: 328,696

[22] Filed: Dec. 8, 1981

[30] Foreign Application Priority Data

Dec. 30, 1980 [JP] Japan .............................. 55-186819
Feb. 6, 1981 [JP] Japan .............................. 56-17214

[51] Int. Cl.$^3$ .................. C12P 13/04; C12P 7/62; C07B 19/02
[52] U.S. Cl. .................................. 435/106; 435/135; 435/280; 435/830; 435/832; 435/840; 435/843; 435/859; 435/872; 435/874; 435/882; 435/885; 435/911; 435/912; 435/913; 435/921; 435/929; 435/931; 435/932; 435/933; 435/938; 435/939
[58] Field of Search ............... 435/106, 119, 280, 135

[56] References Cited

U.S. PATENT DOCUMENTS 4,242,452 12/1980 Yamada et al. ............... 435/280 X
4,302,541 11/1981 Hirata et al. ..................... 435/119
4,332,905 6/1982 Olivieri et al. ..................... 435/280

OTHER PUBLICATIONS

Ohno et al., Journal American Chemical Society, vol. 103, pp. 2405–2406, (1981).

Primary Examiner—Lionel M. Shapiro
Attorney, Agent, or Firm—Armstrong, Nikaido, Marmelstein & Kubovcik

[57] ABSTRACT

A process is disclosed in which an optically active monoalkyl ester of β-(S)-aminoglutaric acid is prepared by subjecting a dialkyl ester of β-protected aminoglutaric acid to the action of a culture broth, cells, or treated cells of a microorganism capable of stereoselectively hydrolyzing only one of the ester groups in the above-mentioned dialkyl ester to produce an optically active monoalkyl ester of β-protected (S)-aminoglutaric acid, and then removing the amino-protecting group from the product. An optically active monoalkyl ester of β-(S)-aminoglutaric acid is useful as a starting material for synthesizing β-lactam antibiotics of carbapenem type such as thienamycin.

15 Claims, No Drawings

PROCESS FOR PREPARATION OF AN OPTICALLY ACTIVE MONOALKYL ESTER OF β-(S)-AMINOGLUTARIC ACID

BRIEF SUMMARY OF THE INVENTION

The present invention relates to a process for preparation of optically active monoalkyl esters of β-(S)-aminoglutaric acid.

Optically active monoalkyl esters of β-(S)-aminoglutaric acid are useful as a starting material for synthesizing those β-lactam antibiotics of carbapenem type such as thienamycin which require an optical activity; therefore, development of an easy and inexpensive method for preparing the optically active esters has been waited for. M. Ohno, one of the inventors of the present invention, and others have developed a method for preparation of an optically active monomethyl ester of β-(S)-aminoglutaric acid (VI) in which an optically inactive dimethyl ester of β-benzyloxyloxycarbonylaminoglutaric acid (IV) is asymmetrically hydrolyzed with esterase derived from the pig liver to prepare an optically active monomethyl ester of β-(S)-benzyloxycarbonylaminoglutaric acid (V) and then the product is subjected to catalytic hydrogenolysis to remove the benzyloxycarbonyl group to obtain the desired product.

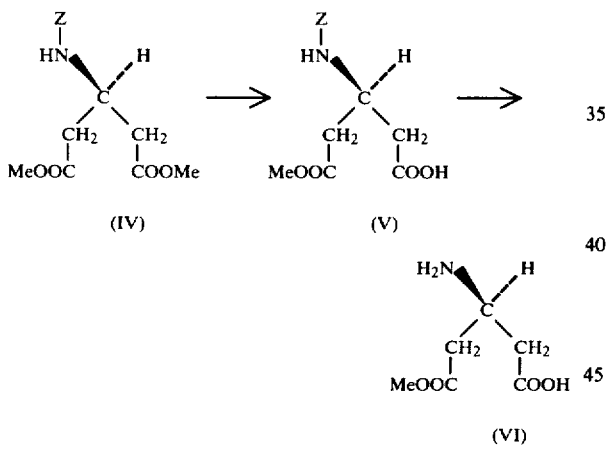

wherein Z represents

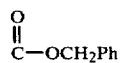

and Me represents CH₃ (Ohno et al., Japanese patent application No. 146344/1980; Ohno et al. J. Am. Soc. 1981, 103, 2405~2406)

The present inventors have thus carried out investigations into a method suitable for mass-production of optically active monoalkyl esters of β-(S)-aminoglutaric acid in which asymmetrical hydrolysis is carried out with microorganisms; as a result, the present inventors have found that there are many microorgnisms capable of stereospecifically hydrolyzing only one of the ester groups of β-protected dialkyl esters of aminoglutaric acid to transform the diesters into monoalkyl esters of β-protected (S)-aminoglutaric acid.

The present invention relates to a process for preparation of an optically active monoalkyl ester of β-(S)-aminoglutaric acid represented by the formula (I):

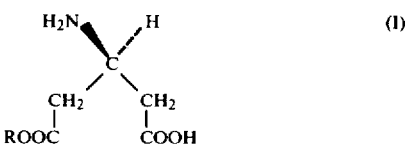

wherein R represents an alkyl having 1~4 carbon atoms, which comprises subjecting a dialkyl ester of β-protected aminoglutaric acid represented by the formula (II):

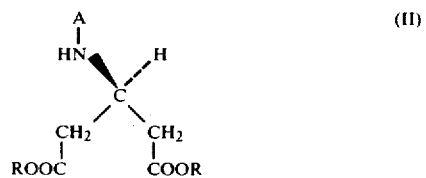

wherein R represents the same as defined above and A represents an amino-protecting group removable by catalytic hydrogenolysis or mild hydrolysis, to the action of a culture broth, cells, or treated cells of a microorganism which is capable of stereoselectively hydrolyzing only one of the ester groups in said dialkyl ester of β-protected aminoglutaric acid and which belongs to the genus Candida, Pichia, Trichosporon, Geotrichum, Aspergillus, Absidia, Actinomucor, Helincostylum, Mucor, Montierella, Paecilomyces, Zygorhynchus, Fusarium, Cricinella, Cunninghamella, Rhizopus, Penicillium, Proteus, Nocardia, Micrococcus, Hafnia, Brevibacterium, Torulopsis, Debaryomyces, Endomyces, Saccharomycopsis, Cryptococcus, Pachysolen, Sporobolomyces, Syringospora, Corynebacterium, Pseudomonas, Arthrobacter, Bacillus, Staphylococcus, or Streptococcus, to produce an optically active monoalkyl ester of β-protected (S)-aminoglutaric acid represented by the formula (III):

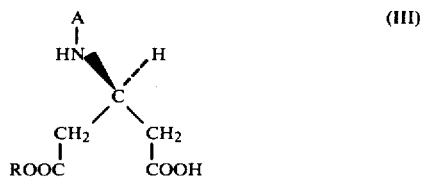

wherein R and A each represents the same as difined above, and then removing the amino-protecting group from the product (III).

DETAILED DESCRIPTION OF THE INVENTION

The amino-protecting group (A) in dialkylesters of β-protected aminoglutaric acid (II) used as a starting compound in the present invention is such one as can be removed by catalytic hydrogenolysis or mild hydrolysis; it thus includes, for example, an aralkyl group such as benzyl and benzhydryl; an aralkyloxycarbonyl group such as benzyloxycarbonyl; a substituted aralkyloxycarbonyl such as p-nitrobenzyloxycarbonyl, p-methoxybenzyloxycarbonyl, p-chlorobenzyloxycarbonyl; and an alkoxycarbonyl group having 4~8 carbon atoms such as t-butoxycarbonyl and t-amyloxycarbonyl.

The starting material, a dialkyl ester of β-protected aminoglutaric acid (II), can be prepared, as shown by the following reaction formula, by reacting a dialkyl ester of 3-ketoglutaric acid (VII) with ammonium acetate to form an unsaturated amine compound (VIII) or (IX) and then reducing this unsaturated amine compound with sodium cyanoborohydride to prepare a dialkyl ester of aminoglutaric acid(III), followed by introducing an amino-protecting group (A) into the amino group of the product (III) (Ohno et al., Japanese patent application No. 146343/1980; Ohno et al., J. Am. Chem. Soc. 1981, 103, 2405~2406).

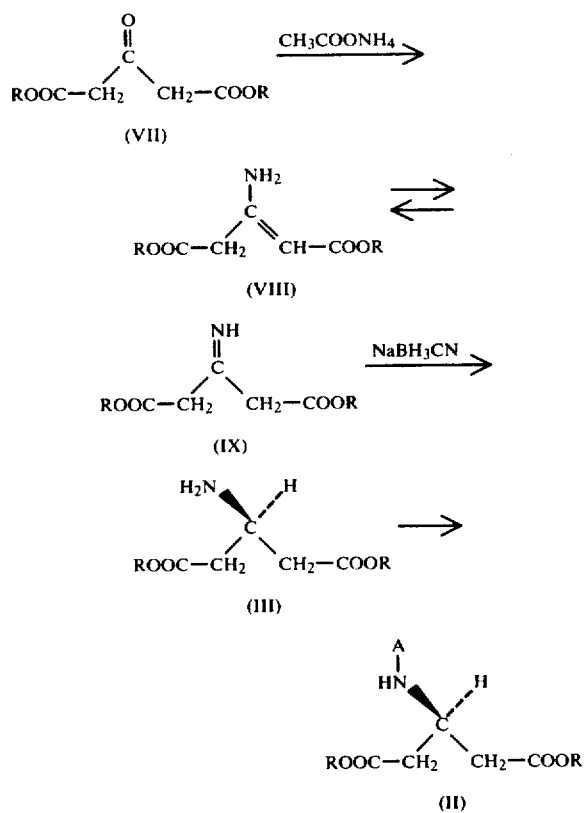

wherein R and A each represents the same as difined above. Alternatively, the starting material (II) can be prepared by synthesizing a dialkyl ester of 3-aminoglutaric acid from a dialkyl ester of malonic acid [H. Fever and W. A. Swarts, J.A.C.S., 77, 5427 (1955)], followed by introducing the amino-protecting group into the product.

As a microorganism, employed in the process of the present invention, which is capable of stereoselectively hydrolyzing only one of the ester groups in a dialkyl ester of β-protected aminoglutaric acid (II), can be cited the following ones: *Candida arborea* IAM 4147, *Candida rugosa* IFO 0750, *Pichia farinosa* IFO 0534, *Trichosporon beigelii* ATCC 22310, *Trichosporon brassicae* IFO 1584, *Geotrichum vanryiae* CBS 439.64, *Aspergillus niger* IAM 3008, *Absidia hyalospora* HUT 1025, *Actinomucor repens* HUT 1049, *Helicostylum nigricans* HUT 1106, *Mucor alternans* HUT 1115, *Mortierella isabellina* HUT 1110, *Paecilomyces varioti* HUT 4018, *Zygorhynchus moelleri* HUT 1305, *Fusarium merismoides* IFO 30040, *Cricinella mucoroides* HUT 1079, *Cunninghamella elegans* HUT 1098, *Mucor javanicus* HUT 1155, *Rhizopus javanicus* HUT 1252, *Penicillium digitatum* IFO 9370, *Proteus mirabilis* IFO 3849, *Nocardia corallina* IFO 3338, *Micrococcus luteus* IFO 12708, *Hafnia alvei* IFO 3731, *Brevibacterium linens* IFO 12142, *Torulopsis candida* IFO 0380, *Torulopsis inconspicua* IFO 0621, *Torulopsis pinus* IFO 0741, *Debaryomyces marama* IFO 0668, *Debaryomyces hansenii* IFO 0794, *Endomyces tetrasperma* CBS 765.70, *Saccharomycopsis lipolytica* IFO 0746, *Cryptococcus albidus* IFO 0378, *Pachysolen tannophilus* IFO 1007, *Sporobolomyces salmonicolor* IAM 12249, *Syringospora claussenii* IFO 0759, *Corynebacterium sepedonicum* IFO 13763, *Corynebacterium xerosis* IFO 12684, *Pseudomonas riboflavian* IFO 13584, *Pseudomonas aeruginosa* IFO 13130, *Arthrobacter paraffineus* ATCC 21218, *Bacillus megaterium* ATCC 10778, *Staphylococcus aureus* IFO 3060, *Streptococcus faecalis* IFO 12964.

IAM: Institute of applied Microbiology, the University of Tokyo, Tokyo, Japan
IFO: Institute for Fermentation, Osaka, Japan
HUT: the Faculty of Engineering, the University of Hiroshima, Hiroshima, Japan
ATCC: the American Type Culture Collection, U.S.A.
CBS: Centraalbureau voor Schimmelcultures Baarn, the Netherlands The cultivation of these microorganisms is usually carried out in a liquid medium but can also be carried out by a solid surface culture. As a cultivation medium, there is used one to which organic carbon sources, nitrogen sources, vitamins, and mineral sources are suitably incorporated. The cultivation is carried out at a temperature of 20°~50° C. and at a pH of 3~11. The growth of microorganisms can be promoted by aeration and stirring.

The stereoselective hydrolysis of the substrate, dialkyl esters of β-protected aminoglutaric acid, by the action of microorganisms can be carried out either by (1) a method in which the hydrolysis is conducted in parallel with the cultivation of microoorganisms by adding the substrate to the cultute medium at the beginning of the cultivation or by (2) a method in which the hydrolysis is carried out by bringing the substrate into contact with a culture broth, cells or treated cells of microorganisms obtained by previously cultivating the microorganisms. From the standpoint of the recovery of the product after completion of the reaction, it is desirable to add the substrate to a highly concentrated cell suspension obtained by concentrating a culture broth of microorganisms by means of centrifugation and so forth. To serve the convenience of the treatment, cells of microorganisms can also be employed in their lyophilized state; they can further be employed as a homogenate or a cell-free extract.

The concentration of the substrate, a dialkyl ester of β-protected aminoglutaric acid, in the reaction mixture may be from 0.01% to as high as about 50%.

Although dialkyl esters of β-protected aminoglutaric acid, as a rule, hardly dissolve in water, this fact does not hinder the present reaction when the contact of the substrate with a culture broth, cells, or treated cells of a microorganism is sufficiently maintained by stirring; however, better results are obtained by adding a water-miscible solvent such as acetone or a surface active agent such as Triton X-100 (polyethylene glycol alkyl aryl ether) and Tween 80 (sorbitan monooleate polyoxyalkylene) to the medium to such an extent that it does not hinder the reaction.

The pH at the time of the stereoselective hydrolysis reaction with microorganisms is 3~11, preferably 6~8. When the reaction is carried out at high concentrations of cells, however, it is desirable to keep the pH at an optimal value by addition of a suitable neutralizing reagent since the pH drops as the product, a monoalkyl ester of β-protected (S)-aminoglutaric acid (III), gradually accumulates in the reaction medium. The temperature of the stereoselective hydrolysis reaction is adopted so as to suit the microorganism employed, being usually 15°~50° C.

Monoalkyl esters of β-protected (S)-aminoglutaric acid (III) produced by the stereoselective hydrolysis reaction can be isolated from the reaction mixture by an ordinary procedure. For example, after insoluble substances such as cells have been removed by centrifugation, the reaction mixture is adjusted to pH 1 and extracted with ethyl acetate. The ethyl acetate extract, dried over anhydrous sodium sulfate, is concentrated to afford an oily monoalkyl ester of β-protected (S)-aminoglutaric acid (III). The product is purified by silica gel column chromatography developed by a suitable solvent. Removal of the solvent from the eluate leaves crystals of a monoalkyl ester of β-protected (S)-aminoglutaric acid (III).

Then, the amino-protecting group (A) of the product (III) is removed by catalytic hydrogenolysis or mild hydrolysis to prepare the desired compound (I).

When the amino-protecting group (A) is an aralkyl, aralkyloxycarbonyl, or substituted aralkyloxycarbonyl group it can be removed by catalytic hydrogenolysis, while when it is an alkoxycarbonyl group having 4~8 carbon atoms it can be removed by mild hydrolysis.

The catalytic hydrogenolysis is carried out by contacting the compound (III) with hydrogen gases in a solvent such as a lower aliphatic alcohol, e.g. methanol and ethanol, and a mixture of the lower aliphatic alcohol with water in the presence of a catalyst such as palladium charcoal (5~20%) and palladium black (5~20%) at an ambient temperature and pressure for from 30 minutes to 2 hours. After the completion of the catalytic hydrogenolysis, the product (I) can be isolated as powders by filtering the reaction mixture followed by concentration of the filtrate.

The mild hydrolysis, on the other hand, is carried out either by reacting the compound (III) with hydrogen chloride in an organic solvent such as ethyl acetate, ethanol, acetic acid, and dioxane at room temperature for from 30 minutes to 1 hour or by reacting the compound (III) with trifluoroacetic acid in anisole or in the absence of a solvent at room temperature for from 30 minutes to 2 hours. After the completion of the hydrolysis, the product (I) can be isolated by removing the solvent and the acid by concentration followed by ion exchange chromatography.

The present invention will next be explained in detail by examples, but it is in no way limited to these examples.

EXAMPLE 1

An aqueous nutrient medium having the following composition was prepared:

(Composition of the medium)

glucose 4%, yeast extract 0.3%, meat extract 0.3%, peptone 0.3%, $(NH_4)_2PO_4$ 0.2%, $KH_2PO_4$ 0.1%, pH 7.0

Each 400 ml of the medium was poured into a 2-L shaking flask and sterilized at 120° C. for 15 minutes.

The culture medium in the shaking flask was inoculated with each 10 ml of seed cultures of microorganisms shown in table 1 which had previously been cultivated in a medium having the same composition as described above. The inoculated culture medium was incubated with shaking at 30° C. for 24 hours. Ten cultivations were made for each strain to obtain each 4 l of culture broth. Cells were harvested from the culture broth by centrifugation. To a suspension of cells in 1 L of M/15 phosphate buffer (pH 7.0) was added a solution of 3 g dimethyl ester of β-benzyloxycarbonylaminoglutaric acid in 30 ml of acetone. The mixture was placed in a 3-L mini-jar fermenter, and the reaction was carried out at 30° C. for 6 hours.

After the completion of the reaction, a supernatant obtained by centrifugation was adjusted to pH 1 and extracted with 2 L of ethyl acetate. After the extract had been dried over anhydrous sodium sulfate, the solvent was evaporated under reduced pressure. The residue was charged onto a silica gel column prepared by suspension of silica gel in benzene and eluted with a mixture of bezene/acetone (10:1). Fractions of monomethyl ester of β-benzyloxycarbonylaminoglutaric acid were collected, and the solvent was evaporated under reduced pressure to afford white crystals of monomethyl ester of β-benzyloxycarbonylaminoglutaric acid. The NMR spectrum and the RF value on silica gel thin layer chromatogram (ethyl acetate:ethanol:water=5:1:1) were in agreement with those of an authentic sample prepared according to the Ohno's method using esterase derived from the pig liver (Japanese patent application No. 146344/1980). The specific rotation of all the products for each microorganism was in the range of $[\alpha]_D^{25} = +0.55° \sim 0.71°$ (C=6, CHcl$_2$), showing that they are all monomethyl ester of β-(S)-benzyloxycarbonylaminoglutaric acid.

In 20 ml of methanol was dissolved 200 mg of the monomethyl ester obtained above. The solution, after addition of 40 mg of 10% palladium charcoal, was stirred in a hydrogen atmosphere for 30 minutes. The reaction mixture was filtered and concentrated to afford 75~97 mg of white crystals of monomethyl ester of β-(S)-aminoglutaric acid, of which the NMR spectrum was in agreement with that of an authentic sample and of which the specific rotation was $[\alpha]_D^{25} = -5.40° \sim 5.61°$ (C=3, H$_2$O).

TABLE 1

| Strain | Yield of monomethyl ester of β-(S)-benzyloxy-carbonyl-glutaric acid (mg) | Yield of*[1] monomethyl ester of β-(S)-aminoglutaric acid (mg) |
|---|---|---|
| *Candida arborea* IAM 4147 | 2150 | 93 |
| *Candida rugosa* IFO 0750 | 457 | 85 |
| *Pichia farinosa* IFO 0534 | 1940 | 97 |
| *Trichosporon beigelli* ATCC 22310 | 415 | 75 |
| *Trichosporon brassicae* IFO 1584 | 383 | 79 |
| *Geotrichum vanryiae* CBS 439.64 | 970 | 82 |
| *Aspergillus niger* IAM 3008 | 230 | 76 |
| *Absidia hyalospora* HUT 1025 | 421 | 95 |
| *Actinomucor repens* | 290 | 75 |

TABLE 1-continued

| Strain | Yield of monomethyl ester of β-(S)-benzyloxy-carbonyl-glutaric acid (mg) | Yield of*[1] monomethyl ester of β-(S)-aminoglutaric acid (mg) |
|---|---|---|
| HUT 1049 | | |
| helicostylum nigricans HUT 1106 | 301 | 83 |
| Mucor alternans HUT 1115 | 246 | 89 |
| Mortierella isabellina HUT 1110 | 532 | 91 |
| Paecilomyces varioti HUT 4018 | 279 | 83 |
| Zygorhynchus moelleri HUT 1305 | 296 | 78 |
| Fusarium merismoides IFO 30040 | 252 | 87 |
| Cricinella mucoroides HUT 1079 | 209 | 85 |
| Cunninghamella elegans HUT 1098 | 754 | 89 |
| Packysolen tannophilus IFO 1007 | 369 | 96 |
| Sporobolomyces salmonicolor IAM 12249 | 568 | 92 |
| Syringospora claussenii IFO 0759 | 492 | 87 |
| Corynebacterium spendonicum IFO 13763 | 396 | 92 |
| Corynebacterium xerosis IFO 12684 | 563 | 91 |
| Pseudomonas riboflavina IFO 13584 | 1956 | 96 |
| Pseudomonas aeruginosa IFO 13130 | 1150 | 95 |
| Arthrobacter paraffineus ATCC 21218 | 976 | 93 |
| Bacillus megaterium ATCC 10778 | 286 | 87 |
| Staphylococcus aureus IFO 3060 | 315 | 94 |
| Streptococcus faecalis IFO 12964 | 425 | 87 |

*[1] Deprotection was carried out by catalytic hydrogenolysis of each 200 mg of monomethyl ester of β-(S)-benzyloxycarbonylaminoglutaric acid obtained by the reaction with each microorganism. The amounts of monomethyl ester of β-(S)-aminoglutaric acid thus obtained are shown.

EXAMPLE 2

Cell suspensions were prepared by each cultivating candida arborea IAM 4147, Pichia farinosa IFO 0534, Geotrichum vanryias CBS 439.64, Torulopsis pinus IFO 0741, Debaryomyces marama IFO 0668, and Pseudomonas riboflavina IFO 13584 in the same manner as in Example 1. To each 1 L of the cell suspensions was added 3 g of dimethyl ester of β-t-butoxycarbonylaminoglutaric acid, and the reaction was carried out in a 3-L mini-jar fermenter with stirring at 30° C. for 6 hours. After the completion of the reaction, the product monomethyl ester of (S)-t-butoxycarbonylaminoglutaric acid was extracted and purified in the same manner as in Example 1. The product was then reacted with 5 cc of trifluoroacetic acid without a solvent at room temperature for 1 hour. The reaction mixture was concentrated under reduced pressure and then the product isolated and purified by ion exchange chromatography to afford white crystals of monomethyl ester of β-(S)-aminoglutaric acid each in amounts shown in Table 2. The NMR spectrum of each of the products was all in agreement with that of an authentic sample and the specific rotation was $[\alpha]_D^{25} = -5.50 \sim 5.61$ (C=3, H$_2$O), thus the products being each confirmed to be monomethyl ester of β-(S)-aminoglutaric acid.

TABLE 2

| Strain | Yield of monomethyl ester of β-(S)-aminoglutaric acid |
|---|---|
| Candida arborea IAM 4147 | 1020 mg |
| Pichia farinosa IFO 0534 | 975 mg |
| Geotrichum vanryiae CBS 439.64 | 867 mg |
| Torulopsis pinus IFO 0741 | 880 mg |
| Debaryomyces marama IFO 0668 | 830 mg |
| Pseudomonas riboflavina IFO 13584 | 958 mg |

EXAMPLE 3

Candida arborea IAM 4147, Pichia farinosa IFO 0534, Geotrichum vanryiae CBS 439.64, Torulopsis pinus IFO 0741, Debaryomyces marama IFO 0668, and Pseudomonas riboflavina IFO 13584 were each cultivated in the same manner as in Example 1 to prepare each 2 L of cell suspension for each strain. Each of the cell suspensions was divided into 2 parts. To the one part of the cell suspensions was added 3 g of diethyl ester of β-benzyloxycarbonylglutaric acid, and to the other part thereof 3 g of diethyl ester of β-t-butoxycarbonylaminoglutaric acid. The reaction was each carried out with stirring in a mini-jar at pH 7.0 and at a temperature of 30° C. for 24 hours. After the completion of the reaction, extraction and purification of the product were carried out in the same manner as in Example 1 and 2 to afford each monoethyl ester of β-benzyloxycarbonylglutaric acid and monoethyl ester of β-t-butoxycarbonylaminoglutaric acid. Deprotection of the each monoethyl ester was carried out in the same manner as in Example 1 and 2 correspondingly to each afford an oily substance in amounts shown in Table 3. The NMR spectrum of the subtance was in agreement with that of an authentic sample of monoethyl ester of β-(S)-amonoglutaric acid. The specific rotation of the substance was $[\alpha]_D^{25} = -3.80° \sim 3.85°$ (C=4, H$_2$O). Thus the substance was confirmed to be monoethyl ester of β-(S)-aminoglutaric acid.

TABLE 3

| Strain | Substrate | Yield of monoethyl ester of β-(S)-aminoglutaric acid |
|---|---|---|
| Candida arborea IAM 4147 | diethyl ester of β-benzyloxy-carbonylamido-glutaric acid | 970 mg |
| Pichia farinosa IFO 0534 | | 850 mg |
| Geotrichum vanryiae CBS 439.64 | | 742 mg |
| Torulopsis pinus IFO 0741 | | 620 mg |
| Debaryomyces marama IFO 0668 | | 590 mg |
| Pseudomonas riboflavina IFO 13584 | | 710 mg |
| Candida arborea IAM 4147 | diethyl ester of β-t-butoxy-carbonylamino-glutaric acid | 732 mg |
| Pichia farinosa IFO 0534 | | 690 mg |
| Gestrichum vanryiae CBS 439.64 | | 703 mg |
| Torulopis pinus IFO 0741 | | 523 mg |
| Debaryomyces marama IFO 0668 | | 465 mg |
| Pseudomonas riboflavina IFO 13584 | | 550 mg |

What is claimed is:

1. A process for preparation of an optically active monoalkyl ester of β-(S)-aminoglutaric acid represented by the formula (I):

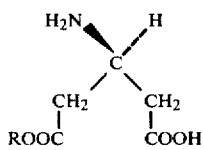

wherein R represents an alkyl having 1~4 carbon atoms, which comprises subjecting a dialkyl ester of β-protected aminoglutaric acid represented by the formula (II):

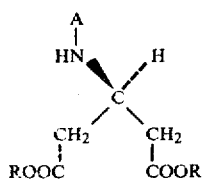

wherein R represents the same as difined above and A represents an amino-protecting group removable by catalytic hydrogenolysis or mild hydrolysis, to the action of a culture broth, cells, or treated cells of a microorganism which is capable of stereoselectively hydrolyzing only one of the ester groups in said dialkyl ester of β-protected aminoglutaric acid (II) and which belongs to the genus Candida, Pichia, Trichosporon, Geotrichum, Aspergillus, Absidia, Actinomucor, Hilicostylum, Mucor, Mortierella, Paecilomyces, Zygorhynchus, Fusarium, Cricinella, Cunninghamella, Rhizopus, Penicillium, Proteus, Nocardia, Micrococcus, Hafnia, Brevibacterium, Torulopsis, Debaryomyces, Endomyces, Saccharomycopsis, Cryptococcus, Pachysolen, Sporobolomyces, Syringospora, Corynebacterium, Pseudomonas, Arthrobacter, Bacillus, Staphylococcus, or Streptococcus, to produce an optically active monoalkyl ester of β-protected (S)-aminoglutaric acid represented by the formula (III):

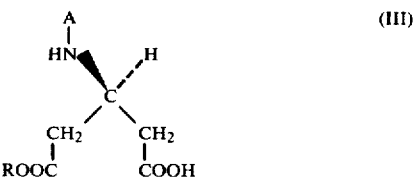

wherein R and A each represents the same as defined above, and then removing the amino-protecting group from the product (III).

2. The process according to claim 1 wherein A represents aralkyl, aralkyloxycarbonyl, substituted aralkyloxycarbonyl, or alkoxycarbonyl having 4~8 carbon atoms.

3. The process according to claim 2 wherein the aralkyl is benzyl or benzhydryl.

4. The process according to claim 2 wherein the aralkyloxycarbonyl is benzyloxycarbonyl.

5. The process according to claim 2 wherein the substituted aralkyloxycarbonyl is p-nitrobenzyloxycarbonyl, p-methoxybenzyloxycarbonyl, or p-chlorobenzyloxycarbonyl.

6. The process according to claim 2 wherein the alkoxycarbonyl having 4~8 carbon atoms is t-butoxycarbonyl or t-amyloxycarbonyl.

7. The process according to claim 1 wherein R represents methyl or ethyl.

8. The process according to claim 1 wherein removal of A is carried out by catalytic hydrogenolysis ot mild hydrolysis.

9. The process according to claim 1 wherein A represents aralkyl, aralkyloxycarbonyl, or substituted aralkyloxycarbonyl and removal of A is carried out by catalytic hydrogenolysis.

10. The process according to claim 9 wherein the catalytic hydrogenolysis is carried out in the presence of palladium charcoal or palladium black as a catalyst.

11. The process according to claim 1 wherein A represents alkoxycarbonyl having 4~8 carbon atoms and removal of A is carried out by mild hydrolysis.

12. The process according to claim 11 wherein the mild hydrolysis is carried out with hydrogen chloride in an organic solvent.

13. The process according to claim 11 wherein the mild hydrolysis is carried out with trifluoroacetic acid.

14. The process according to claim 1 wherein the subjection of the compound (II) to the action of a culture broth, cells, or treated cells of the microorganism is carried out at a pH of 6~8.

15. The process according to claim 1 wherein the subjection of the compound (II) to the action of a culture broth, cells, or treated cells of the microorganism is carried out at a temperature of 15°~50° C.

* * * * *